(12) United States Patent
Oki et al.

(10) Patent No.: US 6,443,939 B1
(45) Date of Patent: Sep. 3, 2002

(54) DEVICE FOR DISPOSING EXCREMENT

(75) Inventors: Nobuyoshi Oki; Syuei Tamura; Hiroshi Sakai; Kimio Sato, all of Tokyo (JP)

(73) Assignee: Niles Parts Company, Ltd. (JP)

( * ) Notice: Subject to any disclaimer, the term of this patent is extended or adjusted under 35 U.S.C. 154(b) by 9 days.

(21) Appl. No.: 09/686,134

(22) Filed: Oct. 11, 2000

(30) Foreign Application Priority Data

Nov. 17, 1999 (JP) ............................................. 11-326415

(51) Int. Cl.⁷ ................................................ A61F 13/15
(52) U.S. Cl. ...................... 604/393; 604/355; 604/334; 604/395; 604/399; 604/402; 4/484
(58) Field of Search ................................. 604/334, 355, 604/358, 393, 395, 399, 400, 402; 2/22, 23, 24; 4/443, 484, 476, 479

(56) References Cited

U.S. PATENT DOCUMENTS

| | | | | |
|---|---|---|---|---|
| 4,614,000 A | * | 9/1986 | Mayer | ............................ 5/484 |
| 5,342,583 A | * | 8/1994 | Son | ............................ 422/107 |
| 5,681,297 A | * | 10/1997 | Hashimoto et al. | ......... 604/355 |
| 5,997,491 A | * | 12/1999 | Harris | ............................ 602/6 |
| 6,067,678 A | * | 5/2000 | Trevino | ........................ 5/628 |

FOREIGN PATENT DOCUMENTS

| | | | | |
|---|---|---|---|---|
| JP | 4-364841 | | 12/1992 | |
| JP | 08/257056 A | * | 3/1995 | ........... A61F/13/00 |
| JP | 10/028697 A | * | 1/1997 | ............. A61F/5/44 |

* cited by examiner

Primary Examiner—John G. Weiss
Assistant Examiner—Jacqueline Stephens
(74) Attorney, Agent, or Firm—Rader, Fishman & Grauer PLLC; Ronald P. Kananen, Esq.

(57) ABSTRACT

A device for disposing excrement is provided which prevents irritation of the skin of a sick person or the like wearing a diaper cup. The device for disposing excrement has a diaper cup main body 2 enclosing a pelvic region of a human body, a discharge port 2d to discharge the excrement excreted in the diaper cup main body 2, an anus wash nozzle to eject liquid for washing away the excrement, sensors 13, 14 to detect the excrement excreted in the diaper cup main body 2, and a changeable diaper 3 removably provided on the diaper cup main body 2. A buffer member 25 is interposed between the diaper cup main body 2 and the changeable diaper 3.

12 Claims, 12 Drawing Sheets

DEVICE FOR DISPOSING EXCREMENT

BACKGROUND OF THE INVENTION

1. Field of the Invention

The present invention relates to devices for disposing excrement of sick persons unable to walk, aged bedridden in hospitals, and the like. More particularly, the present invention relates to a device for disposing excrement which is capable of automatically disposing of the excrement of a sick or bedridden person and washing the places tainted with the excrement.

2. Description of the Related Art

A conventional device for disposing excrement is disclosed, for example, in Japanese Patent Laid-Open No. 364841/1992. The conventional device for disposing excrement has, in a center of a diaper cover, a hole opened to insert through an evacuation pipe to discharge excrement, a pipe to feed warm water, a pipe to feed warm air, and a cord connected to a sensor to detect excrement.

A skin cloth to be attached to the main body has a hole in a surface facing the cup portion. In the left and right side of the skin-cloth hole there are attached respective elongate plate portions firmly fixed with in-line projection buttons so that the skin cloth is attached to the main body through the projection buttons. The main body has, in the cup portion, a washing ejection port, an air-delivery inlet port and an excrement-detecting sensor. The excrement-detecting sensor comprises two feces excrement-detecting sensors arranged extending from around the discharge port to an inside of the discharge port, and three urine excrement-detecting sensors arranged around the discharge port.

However, the conventional device for disposing excrement is limited in its flexibility despite a soft insulative material being employed to meet various body forms. When wearing the diaper cup of the conventional device for a long time, the sick or bedridden person often feels pain due to hardness or the like. Thus, the conventional device suffers from the problem of being uncomfortable when it is worn for a long time.

The conventional device has another problem that, when the sick or bedridden person wears the diaper cup for a long time, skin irritation occurs due to a body weight of the person.

SUMMARY OF THE INVENTION

An object of the present invention is to solve the problems in the conventional device for disposing excrement described above. More specifically, it is an object of the invention to provide a device for disposing excrement which prevents irritation of the skin of the person wearing the diaper cup and is comfortable to wear.

The present invention has been made in order to solve the above-stated problems in the related art. The present invention provides a device for disposing excrement having a diaper cup main body for enclosing a pelvic region of a human body, a discharge port for discharging excrement excreted in the diaper cup main body, a sensor for detecting the excrement excreted in the diaper cup main body, and a changeable diaper removably provided on the diaper cup main body. The excrement disposal apparatus is characterized by a buffer member interposed between a pelvic region of a human body and the diaper cup main body.

The diaper cup main body preferably has a cavity formed in a surface on a side to be fit on a pelvic region of a human body to put a human body in a non-contact state. The buffer member is laid in a peripheral material of the cavity of the diaper cup main body beneath a pelvic region of a human body.

The buffer member preferably comprises a thick plate member.

The buffer member preferably comprises a gel soft material.

The diaper cup main body preferably has a waist-fit seat generally in a plate form provided continuous with an upper end thereof. The buffer member is provided on an upper position of the waste-fit seat.

The buffer member is preferably provided projecting at an upper end of the changeable diaper on a back side of a human body.

The buffer member is preferably provided inserted in a bag provided on an inner side of the changeable diaper to be fit on a human body.

The buffer-member-insertion bag of the changeable diaper is preferably formed by a waterproof cloth on a side of the cavity.

The bag of the changeable diaper into which the buffer member is inserted is preferably arranged with a waterproof sheet in a seam of the waterproof cloth.

The bag of the changeable diaper into which the buffer member is inserted preferably has a magic tape and has a close cover to close an opening.

DETAILED DESCRIPTION OF THE PREFERRED EMBODIMENTS

Preferred embodiments of the present invention will now be explained in detail with reference to FIGS. 1 to 20 of the drawings.

Figure 1:
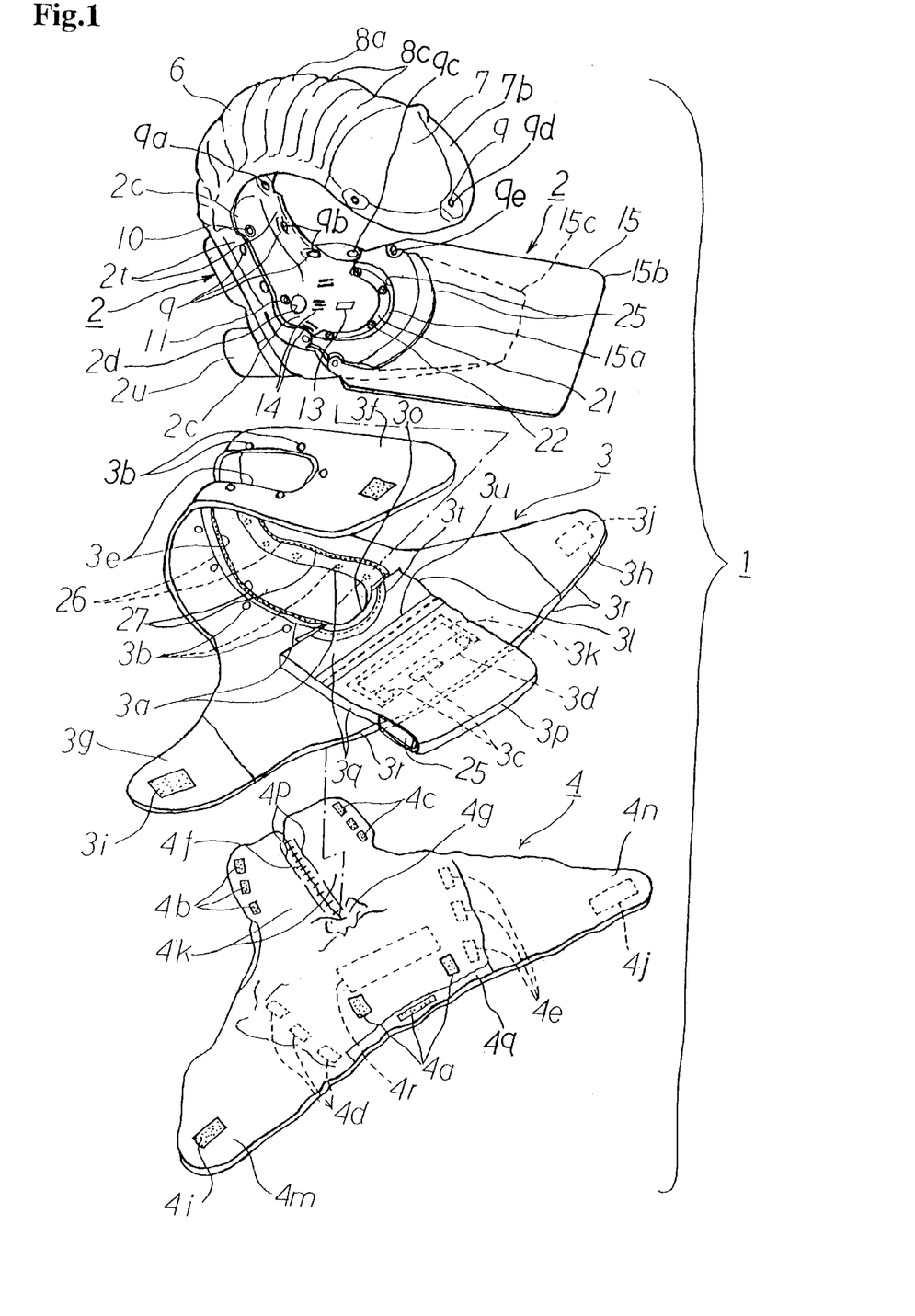
FIG. 1 is a perspective view showing a device for disposing excrement according to an embodiment of the present invention.
Figure 2:
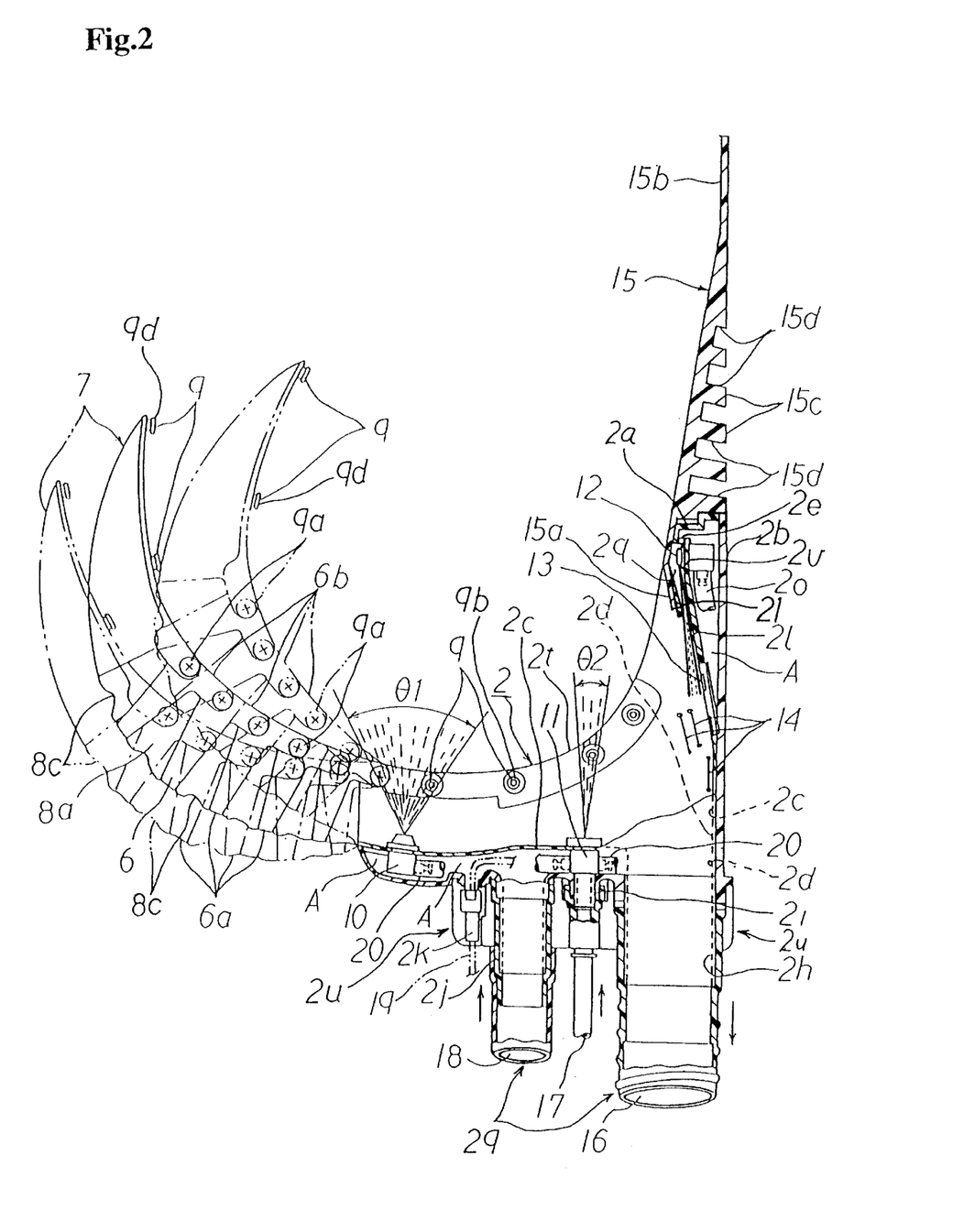
FIG. 2 is a magnified center lengthwise sectional view of a diaper cup main body of the invention.

As shown in FIG. 1, a diaper cup unit 1 comprises a diaper cup main body 2, a changeable diaper 3, and a diaper cover 4. The diaper main body 2, for enclosing a pelvic region of a human body as shown in FIG. 2, is provided continuous with a plurality of concertina joints 6 to have a front cover 7 structured for free bending.

Figure 5:
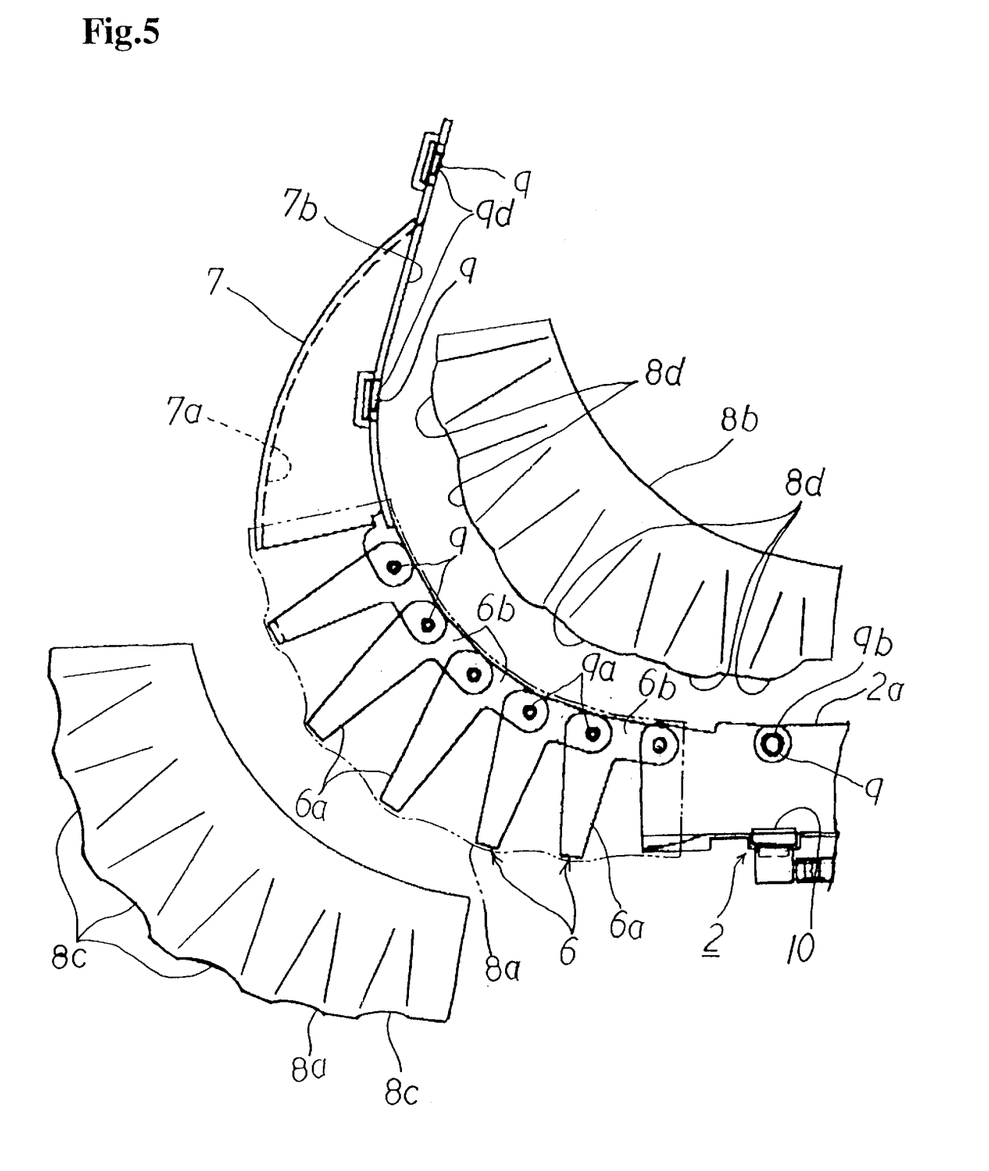
FIG. 5 is a magnified exploded perspective view of concertina joints and waterproof cloth used in the invention.

The concertina joints 6 have inner and outer sides which are respectively covered with waterproof cloths 8a, 8b, as shown in FIG. 5. The cloths 8a, 8b prevent wash water from leaking without interfering with the bending performance of the concertina joints 6. The concertina joints 6 are formed continuous with a cavity 2c, hereinafter described, of the diaper cup main body 2. The concertina joints 6 each comprise a skeleton portion 6a generally in a U-form in section, a connecting portion 6b pivotally supporting each concertina joint 6 for free bending, and pivot holes opened to insert hooks 9a in front and back ends of the connecting portion 6b.

The concertina joints 6 are connected in a continuous manner at each connecting portion 6b by hooks 9 supporting the changeable diaper 3 in the pivot holes. As a result, the concertina joints 6 are allowed to bend and deform, as shown by virtual lines in FIG. 2. The device can thus be fitted on pelvic regions of different sizes to accommodate sick and bedridden persons or the like of various sizes. Also, the front cover 7 forms a curved recess surface 7a continuing a curved surface of the skeleton portion 6a of the concertina joint 6, as shown in FIGS. 1, 2 and 5. The front cover 7 is formed with flanges 7b continuous with the connecting portion 6b of the concertina joint 6, so that the hooks 9d are provided on the flanges 7b.

The waterproof cloths 8a, 8b may be respectively bonded to the whole front and back surfaces, or bonded on front and back surfaces of each of the concertina joints 6. Where the waterproof cloths 8a, 8b are bonded on each concertina joint 6, six waterproof cloths 8a, 8b, for example, are provided continuous on the respective front and back surfaces of the six concertina joints 6 with overlapping bonding points. This allows the waterproof cloths 8a, 8b to be bonded in a bendable and deformable state on the front surface of the concertina joints 6, which is generally spherical in form.

The waterproof cloths 8a, 8b may be formed in one sheet, as shown in FIG. 5. In this case, because the waterproof cloths 8a, 8b are to be bonded on the front and back rounded surfaces of the bend-deformable concertina joints 6, it has spherical areas 8c, 8d formed by pressing a flat strip cloth generally into a spherical form. The waterproof cloths 8a, 8b are also preferably coated with a water preventive agent. The waterproof cloths 8a, 8b are bonded on the concertina portions and skeleton portions 6a of the concertina joints 6 through an adhesive. The waterproof cloths 8a, 8b, if formed in one sheet, can reduce the number of processes of bonding and dry time of the adhesive.

Figure 6:
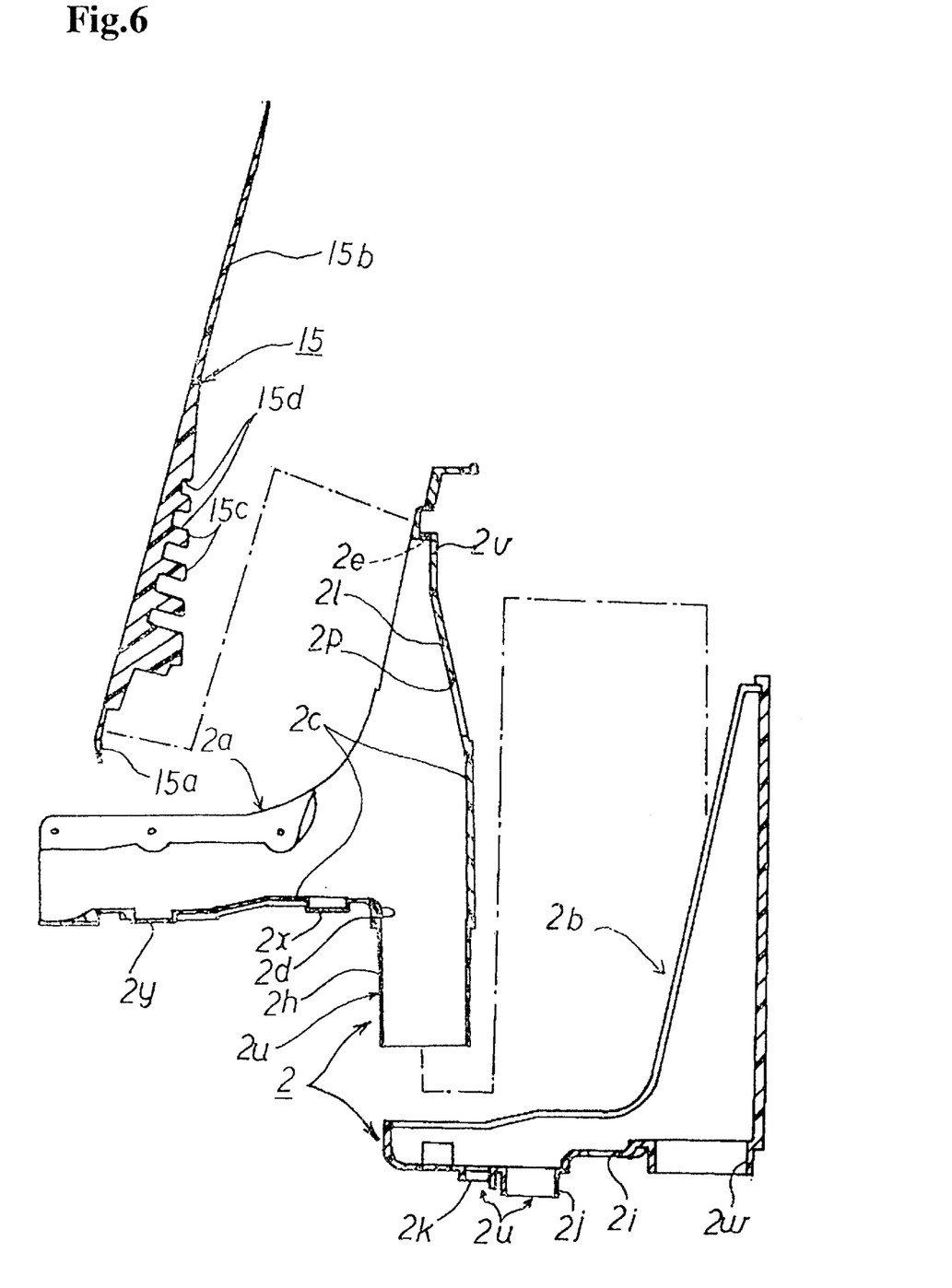
FIG. 6 is an explanatory view of an upper cup, a lower cup and a waist-fit sheet used in the invention.

The diaper cup main body 2, as shown in FIG. 6, is bonded together into one body with an upper cup 2a provided on a side to contact a human body, and a lower cup 2b positioned on an outer side when attached to the human body. The diaper cup main body thus forms a space A at an interior, as shown in FIG. 2. The diaper cup main body 2 is connected into a generally U-form with a front cover 7 to cover a front side of the pelvic region. The diaper cup main body 2 is formed of a hard urethane resin. The concertina joints 6 and a waist-fit seat 15 to cover a back side of the pelvic region are formed of semi-hard urethane resin for covering the entire pelvic region.

The diaper cup main body 2 has hooks 9b, 9c, a private-parts wash nozzle 10, an anus wash nozzle 11, a cup wash nozzle 12, a feces-detecting sensor 13, and a urine-detecting sensor 14, as shown in FIGS. 1 and 2.

The diaper cup main body 2 is connected to an external equipment through use of an excrement-suction hose 16, a wash-water feed hose 17, an air feed hose 18, and a sensor coupler 2k. The excrement-suction hose 16 is used to suck the wash water and excrement in an inside of the diaper cup unit 1. The wash-water feed hose 17 is used to feed wash water to the inside of the diaper cup main body 2. The air feed hose 18 is used to feed warm air to the inside of the diaper cup main body 2. And, the sensor coupler 2k is used to derive electric signals from the feces-detecting sensor 13 and urine-detecting sensor 14.

The upper cup 2a is formed of a hard urethane resin or the like generally in a J-form, as viewed in cross section. The upper cup 2a is arranged, as shown in FIG. 6, with a discharge port 2d provided at a center on a surface side, a connection cylinder portion 2h continuous to the discharge port 2d and connecting to the excrement-suction hose 16, cavities 2c provided on respective sides of the discharge port 2d, nozzle setup holes 2v formed in the cavities 2c to install cup-wash nozzles 12, a nozzle setup hole 2x to install an anus-wash nozzle 11, a nozzle setup hole 2y to install a private-parts wash nozzle 10, a plurality of the hooks 9b in inner upper ends of side walls on left and right sides of the cavity 2c, hooks 9c in left and right edges 2t of the cavity 2c, and air-blow ports 2e, 2f, 2g on a side of the waist-fit seat 15.

The upper cup 2a is formed, in a joining surface on the backside to the lower cup 2b, with inner walls 2m forming the space A to pass air from the connecting cylinder portion 2j to the air blow ports 2e, 2f, 2g through the air feed hose 18. The air entered in the space A through the connecting cylinder portion 2j is branched to the left and right of the connecting cylinder portion 2h connecting to the excrement suction hoses 16, as shown at arrows a and b of FIG. 7. The air entered in the space A is further guided by the inner wall 2m, thus flowing toward the air blow ports 2e, 2f, 2g, as shown at arrows c and d.

Figure 7:
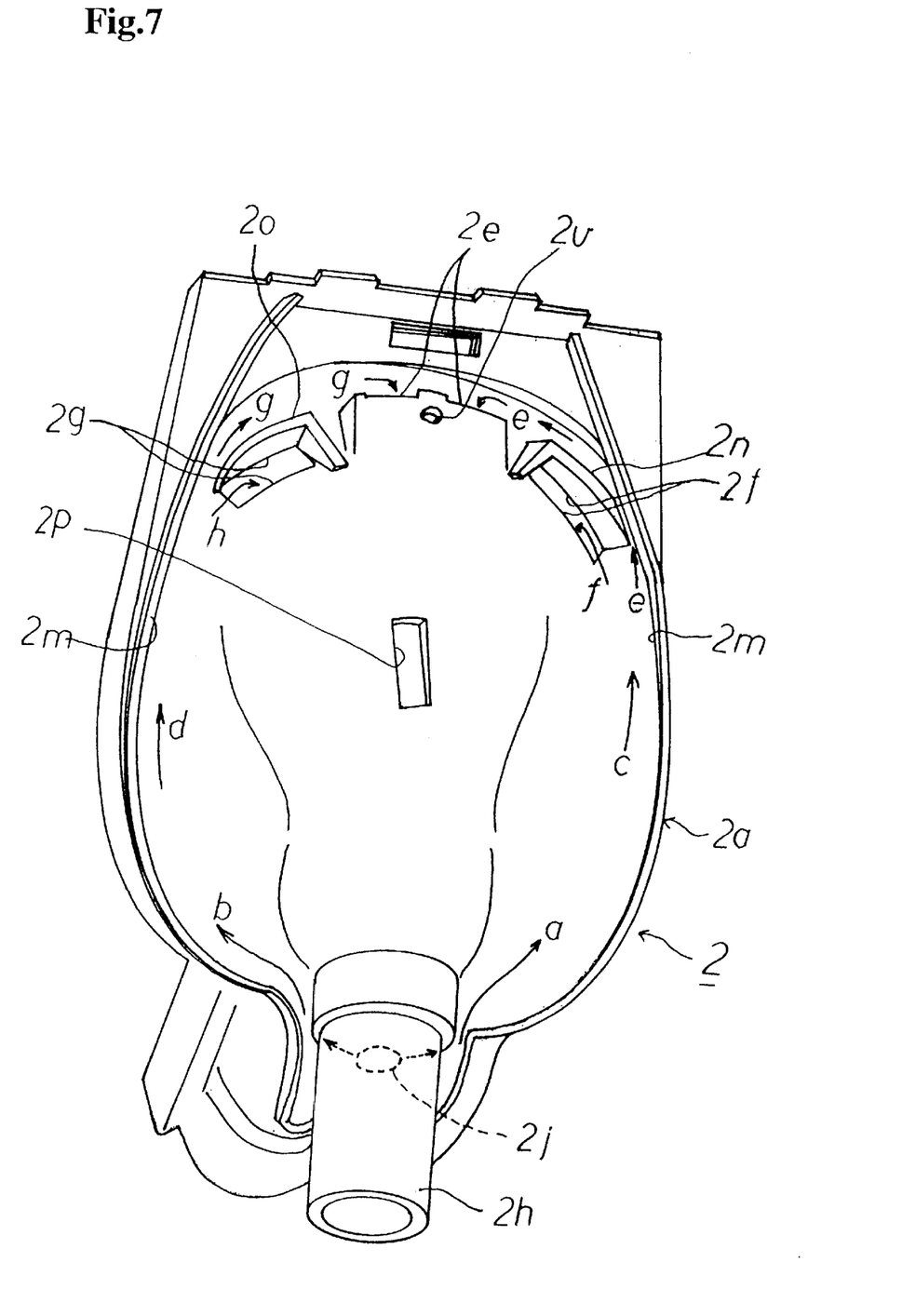
FIG. 7 is a magnified perspective view of the upper cup of the invention.

The air at the arrows c and d, at both left and right, is separated into arrows e and f and arrows g and h, respectively, by a guide wall 2n, 2o generally in an L-form. The air at the arrows e and g flows along the inner wall 2m and passes from the space A to the air hot blow port 2e and then out to a surface of the upper cup 2a. Meanwhile, the air at the arrows f and h is guided on the guide walls 2n and 2o and passes the air blow ports 2f and 2g and then goes out to a surface of the upper cup 2a. A penetration hole 2p, as shown in FIG. 7, is provided for installing a feces-detecting sensor 13.

The guide walls 2n and 2o are walls formed generally in an L-form on center and outer-edge sides of the air blow ports 2f, 2g on the left and right to thereby flow air in equivalent amounts and with good balance through the three air blow ports 2e, 2f, 2g. The guide walls 2n, 2o collect air to the left and right air blow ports 2f, 2g, thereby increasing the amount and intensity of air flow through the left and right air blow ports 2f and 2g.

On a surface side of the air blow ports 2e, 2f, 2g, flaps 21 are fixed through screws 22, as shown in FIGS. 3, 4, 8 and 9. The flaps 21 are guides to increase the intensity of air flow to the surface of the upper cup 2a through the air blow ports 2e, 2f, 2g to reduce air turbulence. The flaps 21 also direct the flow of air from a bottom of the cavity 2c to the discharge port 2d, thereby causing excrement and wash water to flow toward the discharge port 2d with smoothness and efficiency.

Figure 8:
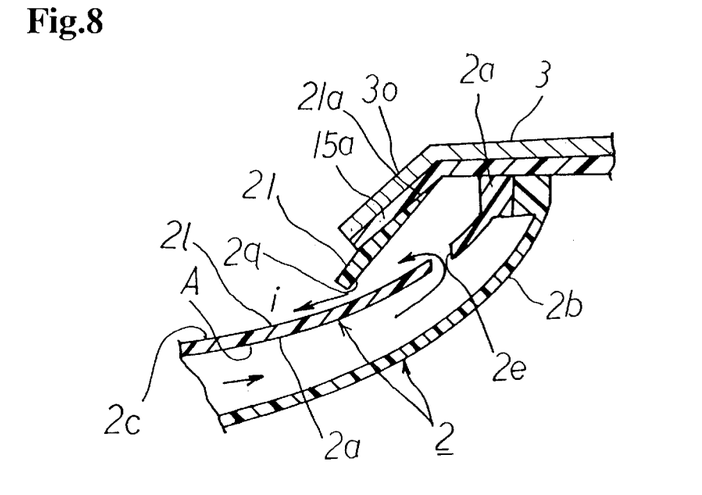
FIG. 8 is a sectional view showing an apron of a changeable diaper of the invention.
Figure 9:
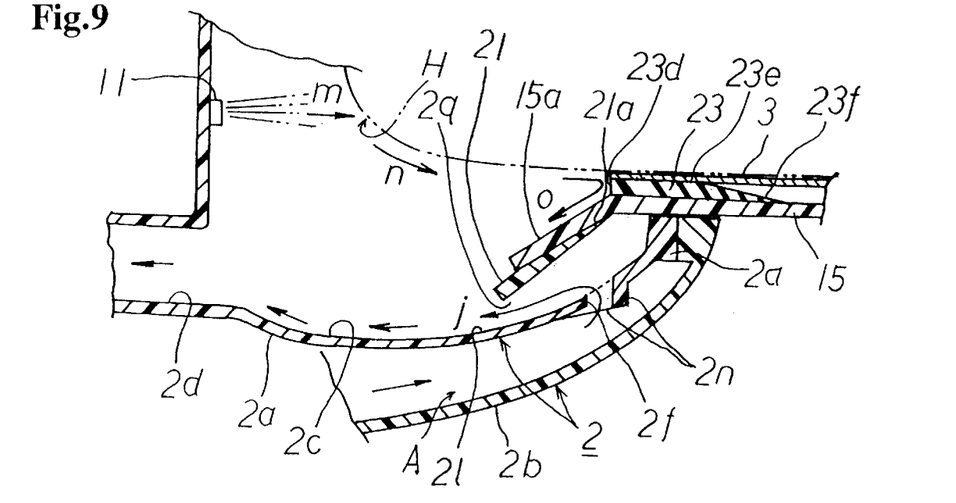
FIG. 9 is a sectional view showing a setup state of a waterproof dam of the invention.

The flap 21 is generally in an arcuate form long in a sideways direction and formed of a semi-hard urethane resin sheet. The flap 21 has a wedge-formed portion 21a on a side of the waist-fit seat 15, as shown in FIGS. 8 and 9. The flaps 21 cover the air blow ports 2e, 2f, 2g, as shown in FIGS. 8 and 9, and are arranged at an upper end in a slant surface 21 of the diaper cup main body 2.

Figure 10:
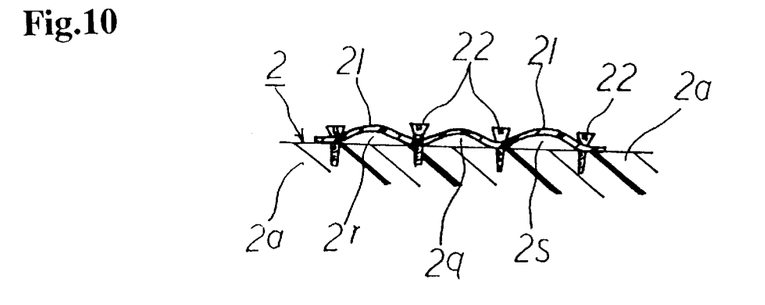
FIG. 10 is a sectional view showing a shape of an outlet port of the invention.

The flap 21 is formed with the wedge-formed portion 21a at one end and the other end directed to the slant surface 21 of the diaper cup main body 2. The flap 21 thereby provides an air blow port 2q, 2r, 2s as a thickness-reduced port. Also, the flaps 21 can make long the shape and decrease the aperture size of the outlet port 2q, 2r, 2s by fixing the side portions of the three air blow ports 3e, 3f, 3g with four screws 22 on a diaper cup main body 2, for example, as shown in FIG. 10. This makes it possible to flow air immediately along a bottom of the entire slant surface 21 and the cavities 2c of the diaper cup main body 2, as indicated by arrows i and j in FIGS. 8 and 9.

Figure 3:
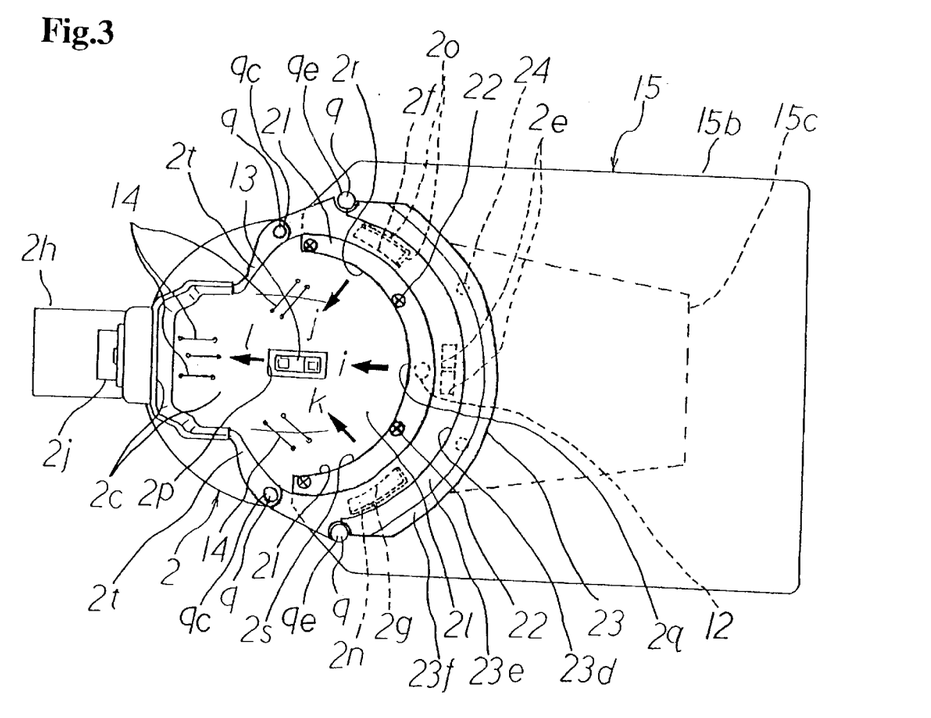
FIG. 3 is a front view of the diaper cup main body of the invention.
Figure 4:
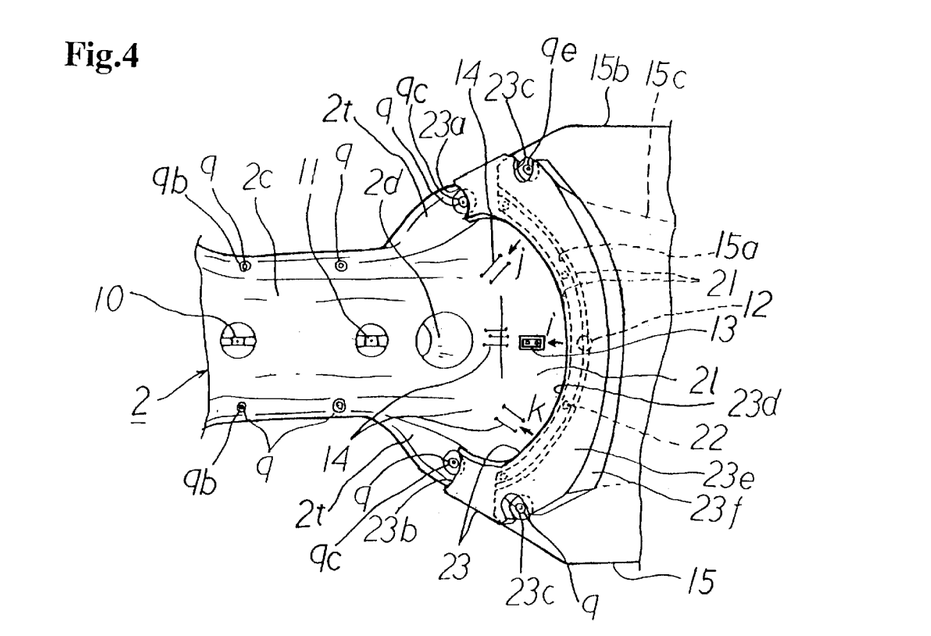
FIG. 4 is a plan view of the diaper cup main body of the invention.

The air blown out of the outlet port 2q, 2r, 2s flows toward the discharge port 2d, as shown at arrows i, j, k, l, because the flap 21 has an arcuate form, as shown in FIGS. 3 and 4. As a result, when a sick person is in a lying state, wash water and urine are splashed smoothly toward the discharge port 2d side, preventing the same from staying in the diaper cup main body 2, and also preventing erroneous operation to discharge urine. Also, feces can be floated and washed, without remainder, out of the cavity 2c of the diaper cup main body 2 by the air from the outlet ports 2q, 2r, 2s and wash water through the anus wash nozzle 11 and cup wash nozzle 12.

Incidentally, the screws 22 in the diaper cup main body 2 are screws made in a same color as the diaper cup main body 2 (e.g., with white paint) so as not to provide a sick person with a feeling of metal mechanical coolness.

A support portion 15a generally in an arcuate form is provided on the flap 21. The support portion 15a is formed at an end of the waist-fit seat 15 to prevent the flap 21 from spreading due to the force of airflow and to provide reinforcement.

Figure 11:
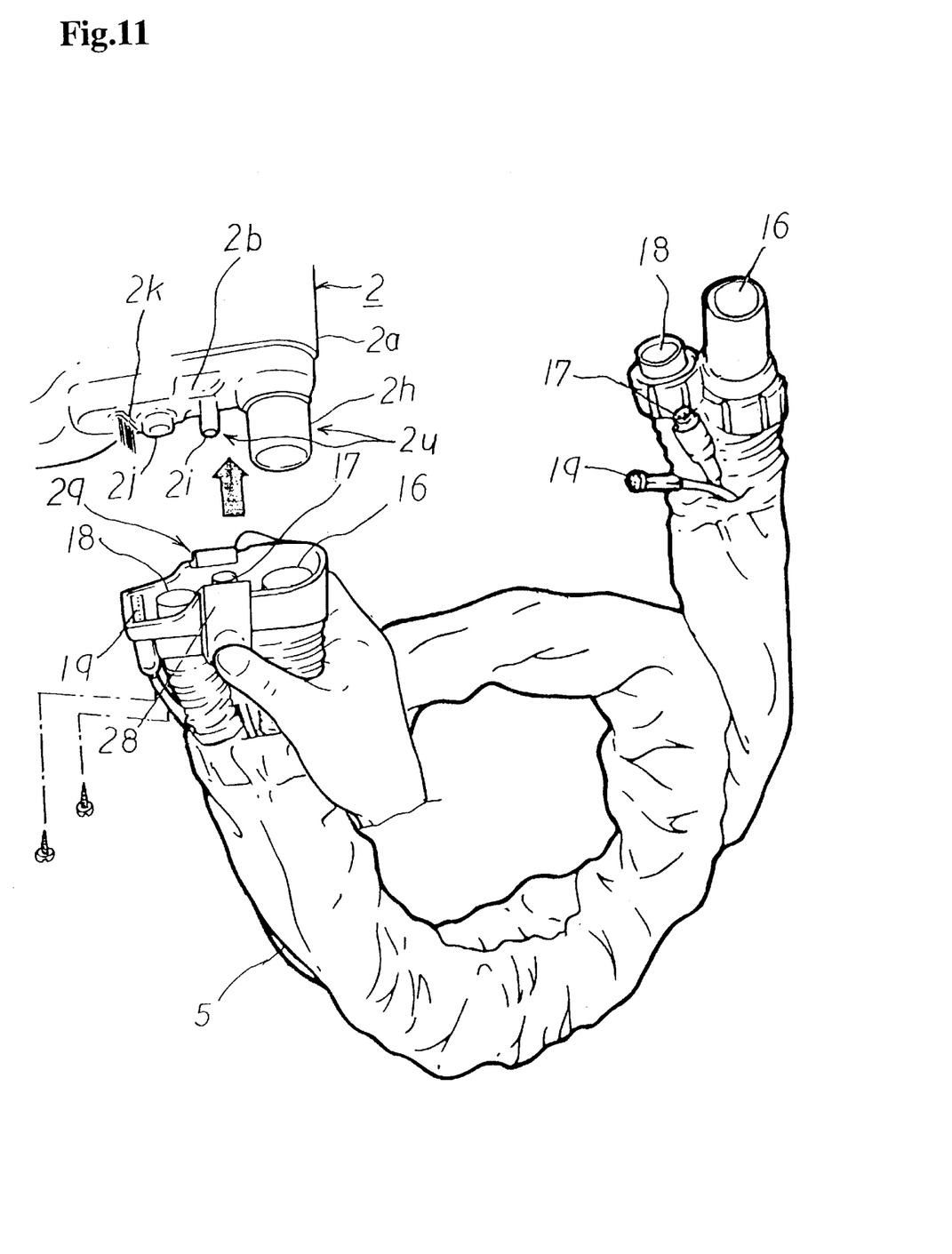
FIG. 11 is a waist-region exploded perspective view showing a structure of a hose connection portion of the diaper main body of the invention.
Figure 12:
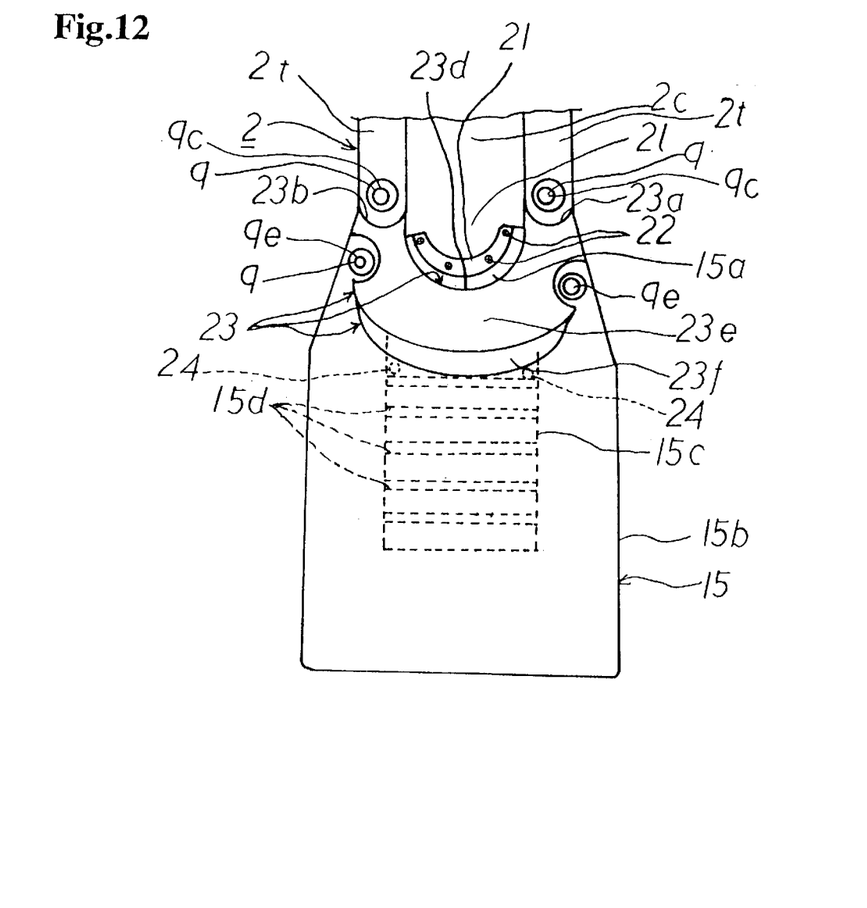
FIG. 12 is a plan view showing a setup state of a waterproof dam of the invention.
Figure 13:
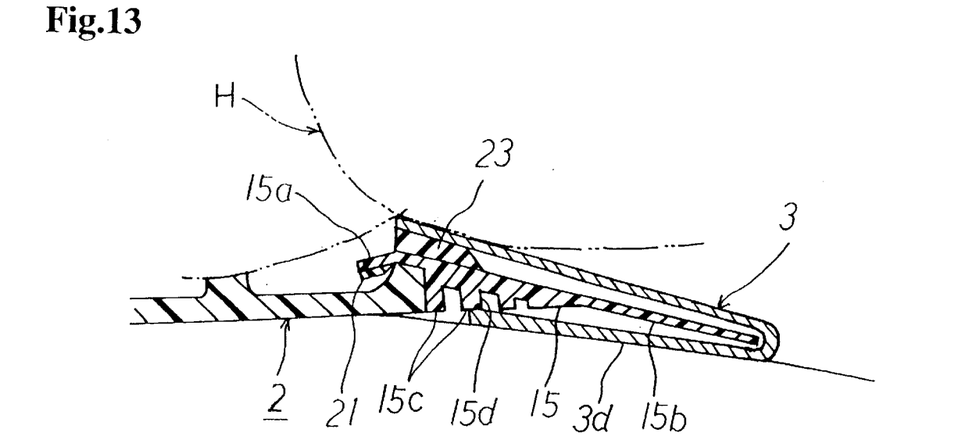
FIG. 13 is a sectional view showing a setup state of a waterproof dam of the invention.

The lower cup 2b of the diaper cup main body 2 is formed of a hard urethane resin similar to the upper cup 2a. As explained above, the lower cup 2b, if joined with an underside of the upper cup 2a, forms a space A with the upper cup 2a. The upper cup 2a and lower cup 2b together form the diaper main body 2. The lower cup 2b is formed, as shown in FIGS. 2, 6 and 11, with a hose connecting portion 2u integrally forming a penetration hole 2w in which the connecting cylinder portion 2h of the upper cup 2a is to be fitted. The lower cup 2b also has a connecting portion 2i to connect between a wash-water feed hose 17 and a water feed pipe 20, a connecting cylinder portion 2j to connect an air-feed hose 18 to feed air into the space A, and a sensor coupler 2k to connect to a cord 19 connected to a power supply or the like.

The excrement suction hose 16 is connected to a vacuum motor or vacuum pump (not shown) by way of an excrement tank (not shown) and vacuum hose (not shown). The wash-water feed hose 17 is connected to a wash-water ejection adjust valve (not shown). The air feed hose 18 is connected to the vacuum motor or vacuum pump. The sensor coupler 2k is connected to a sequencer (not shown) through a sensor signal line (not shown).

Incidentally, the vacuum motor or vacuum pump is accommodated, together with a filter box, air discharge pipe and motor-cooling air suction pipe, in a housing. Also, the excrement suction hose 16 and the wash-water feed hose 17 are coupled together by a drain valve, and the warm water tank is connected with a water discharge valve.

As shown in FIG. 2, the space A provides a space to lay a water feed pipe 20 connected to the private-parts wash nozzle 10, the anus wash nozzle 11, and the cup wash nozzle 12. The space A also provides a space to lay a cord 19 connected to a feces-detecting sensor 13 and urine-detecting sensor 14, and functions as a feed air pipe to feed the air from the air feed hose 18 to the air blow ports 2e, 2f, 2g.

The cavity 2c is a semispherical recess formed in the upper cup 2a, which is formed continuous with a slant surface 21 on the side of the waist-fit seat 15, as shown in FIG. 2. The cavity 2c is arranged, in its bottom surface, with the private-parts wash nozzle 10, the anus wash nozzle 11, the feces-detecting sensor 13, and the urine-detecting sensor 14. Also, around the cavity 2c and in the front cover 7 are provided in line a plurality of hooks 9 comprising hooks 9a, 9b, 9c, 9d, 9e to attach and detach the changeable diaper 3.

The private-parts wash nozzle 10 and the anus wash nozzle 11 are nozzles used exclusively for individually washing the private parts and anus, respectively, of a sick person wearing the diaper cup unit 1, as shown in FIG. 2. The ejection range $\theta 1$ of the private-parts wash nozzle 10 is set wide as compared to the ejection range $\theta 2$ of the anus wash nozzle 11.

The cup wash nozzle 12 is a nozzle to wash away the excrement excreted by a sick person, as shown in FIG. 2, which is arranged on an inner side of the flaps 21 in the vicinity of the air blow port 2e for blowing warm air. The cup wash nozzle 12 operates to eject wash water toward the side of the feces-detecting sensor 13. The cup wash nozzle 12 is fitted in a nozzle setup hole 2v opened in a center nearby the right and left air blow ports 2e, as shown in FIG. 7.

The feces-detecting sensor 13 is a sensor to detect the feces excreted by a sick person or the like. The feces-detecting sensor 13 comprises, for example, one sensor installed at a center location in the slant surface 21, as shown in FIGS. 2 to 4.

The urine-detecting sensor 14 is a sensor to detect the urine excreted by a sick person or the like. As shown in FIGS. 1 to 4, sensors comprising, for example, two to three conductor wires are installed, for example, at three locations. A first location for the sensors is from the air blow ports 2e, 2f, 2g to a center of the cavity 2c in the vicinity of the lower discharge port 2d. Other locations for the sensors are on the side walls at the left and right sides of the lower discharge port 2d and directed toward the discharge port 2d.

The waist-fit seat 15 is a plate on which a sick person or the like rests his or her waist. The seat 15 is formed of semi-hard urethane resin having a hardness, for example, of approximately 70 [Hs]. The waist-fit seat 15 is formed integral with a flat, bendable or deformable plate portion 15*b*, a support portion 15*a* formed on a side of the plate portion 15*b* facing the cavity 2*c*, and a slant portion 15*c* installed in an outward center.

The waist-fit seat 15 has an inner surface which is slanted in its entirety due to the slant portion 15*c* provided in the outer center. The slant portion 15*c* is formed with a plurality of cutout grooves 15*d* which extend laterally and provide a structure that is easy to bend or deform. The waist-fit seat 15 is easy to deform due to the cutout grooves 15*d* so that a sick person or the like wearing the diaper main body 2 can easily and freely change his or her position. Thus, the sick person or the like can rise from the bed easily. The waist-fit seat 15 is fixed to the diaper main body 2 through adhesive and further firmly fixed by screws 24.

A waterproof dam 23 having a generally arcuate form is arranged around the support portion 15*a* of the waist-fit seat 15 where a coccyx is positioned when the diaper cup main body 2 is worn by a sick person or the like. The waterproof dam 23 comprises a buffer member, for example, of silicone rubber having a hardness of approximately 7 [Hs]. The waterproof dam 23 provides a buffer member in a position that a coccyx of a sick person abuts against, and also prevents wash water or urine from leaking outside the diaper cup main body 2.

In the waterproof dam 23, when the wash water ejected in a direction of arrow m through the anus wash nozzle 11 hits a pelvic region H of a sick person or the like, as shown in FIG. 9, the water with the impetus flows in a direction of arrow n along a surface of the pelvic region H to hit against the waterproof dam 23. The wash water hitting the waterproof dam 23 then hits an end of the waterproof dam 23 and is repelled back in a direction of arrow o to flow through the slant surface 21 of the diaper cup main body 2. Then, the wash water flows together with the air flow in the direction of arrows i, j and k from the exit ports 2*q*, 2*r* and 2*s* and toward the discharge port 2*d*.

The waterproof dam 23 comprises, as shown in FIG. 4, opposite ends 23*a*, 23*b* rested on opposite bank-like edges 2*t* on both sides of the cavity 2*c* and matched to a half periphery of the hook 9*c*. The waterproof dam 23 also has a hook buffer portion 23*c* covering a half periphery of another hook 9*e*, an arcuate dam portion 23*d* that meets an outer edge of the slant surface 21 of the diaper cup main body 2, a flat surface portion 23*e* that receives the load of a sick person or the like, and a slant portion 23*f* formed continuous with the flat surface portion 23*e*. The waterproof dam 23 is fixed through adhesive on the diaper cup main body 2 and the waist-fit seat 1S.

The ends 23*a*, 23*b* of the waterproof dam 23 provided at both edges 2*t* of the diaper cup main body 2 provide a waterproof effect of eliminating a gap between a pelvic region H of a sick person or the like and the diaper cup main body 2, thereby preventing wash water or urine from leaking. Also, the ends 23*a*, 23*b* and buffer portion 23*c* prevent the hooks 9*c*, 9*e* provided on the diaper cup main body 2 and the waist-fit seat 15 from abutting against a sick person or the like, thereby preventing irritation of the skin of the sick person or the like.

The dam portion 23*d* reflects wash water or urine. The dam portion 23*d* comprises a soft material and provides a close contact between the waist-fit seat 15 and the changeable diaper 3, thereby preventing the water content from intruding through between the waist-fit seat 15 and the changeable diaper 3. This prevents against wetting in the diaper cover 4 or bed sheet. When receiving a body weight of a sick person or the like, the flat surface portion 23*e* and slant portion 23*f* will not irritate the skin of the sick person or the like, because the waterproof dam 23 is formed of a soft material.

The changeable diaper 3 of the invention will now be described. The changeable diaper 3 has, as shown in FIG. 1, an elongate hole 3*e* opened in a center to insert the hose connecting portion 2*u*, a side-leak preventive frill 3*a* provided on left and right sides of the elongate hole 3*e*, a magic tape 3*c* (for example, a fastening tape available under the trademark VELCRO) to be joined with a corresponding magic tape 4*a* of the diaper cover 4, a bag 3*d* into which the waist-fit seat 15 is to be inserted, a waist cover 3*k* for resting on the waist of a sick person or the like, and a bag 3*l* into which the buffer member 25 is to be inserted.

The changeable diaper 3 is attached by engaging between the hook 9 having the hooks 9*a*, 9*b*, 9*c*, 9*d*, 9*e* on the inner side of the diaper cup main body 2 and the hook 3*b* provided around the elongate hole 3*e*, thereby being wound around the pelvic region H of a sick person or the like. The changeable diaper 3 is provided around the cavity 2*c* of the diaper cup main body 2, and comprises a wrap portion 3*f* provided around the cavity 2*c* of the diaper cup main body 2 to cover the pelvic region H of a sick person or the like, and tightening strip portions 3*g*, 3*h* for turning the waist of the sick person or the like. The changeable diaper 3 is formed, for example, of a nylon cloth material generally in a T form in its entirety.

Figure 14:
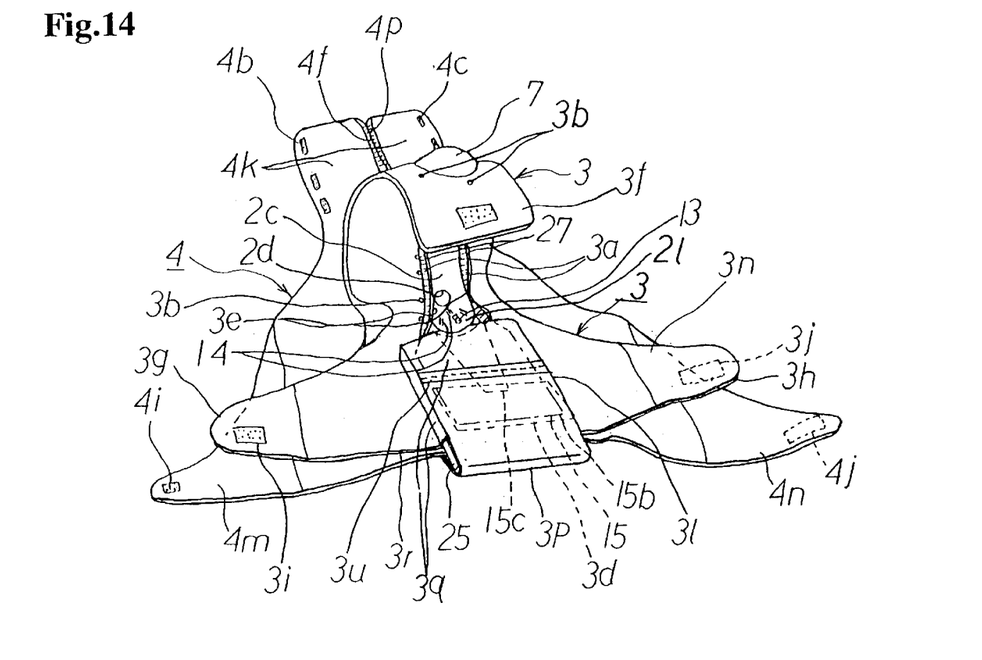
FIG. 14 is a perspective view showing an assembling state of the invention.

The side-leak preventive frills 3*a* are provided on both sides of the elongate hole 3*e* on the inner side of the changeable diaper 3 in a manner covering a head of the hook 3*b*, as shown in FIGS. 1 and 14. The side-leak preventive frill 3*a* is formed, for example, of a waterproof-treated nylon cloth and sewed with corrugation for expansion and contraction. The left and right side-leak preventive frills 3*a* have, at their ends, respective waterproof cloths 27 internally provided with a rubber string 26, as shown in FIG. 18.

Figure 18:
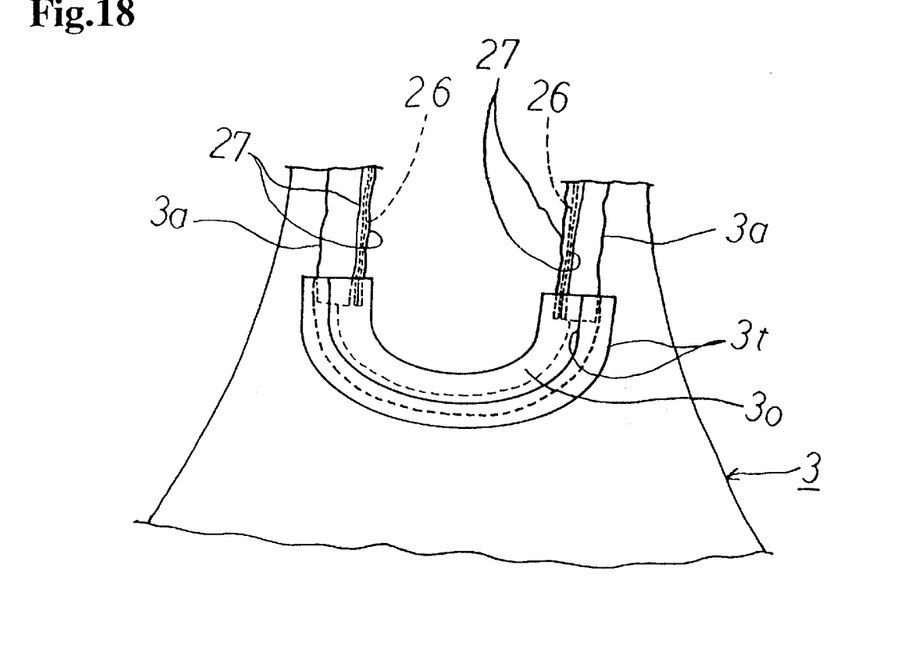
FIG. 18 is a plan view showing a setup state of the apron of the invention.
Figure 19:
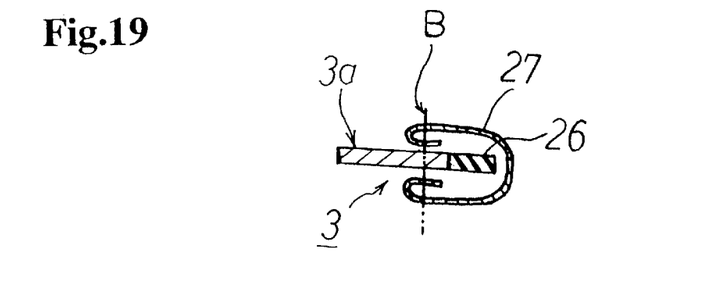
FIG. 19 is a sectional view showing a setup state of a rubber string of the invention.

The rubber string 26 is sewed in an end of the side-leak preventive frill 3a, as shown in FIGS. 18 and 19. The rubber string 26 is covered by waterproof cloth 27, and sewed to the side-leak preventive frill 3*a* by a waterproof thread B with the waterproof cloth 27 bent at its both ends. This prevents against wetting in an outer side of the changeable diaper 3 or diaper cover 4 due to the rubber string 26 having a nature of absorbing and conveying water content.

The hook 3*b* is firmly fixed, for example, in a hole opened around the elongate hole 3*e* in the changeable diaper 3, by press-fitting the members on the front and back sides. The hook 3*b* is provided in a hidden state at the rear of the side-leak preventive frill 3*a* on the inner side of the changeable diaper 3, as shown in FIGS. 1 and 14. The hook 3*b* fits with the hooks 9*b*, 9*c*, 9*e* provided around the cavity 2*c* of the diaper cup main body 2, the hook 9*a* provided at the edge of the concertina joints 6 continuing to the cavity 2*c*, and the hook 9*d* provided at the flange 7*b* of the front cover 7 continuing to the concertina joints 6, thereby fixing the changeable diaper 3. The magic tapes 3*c*, 3*i*, 3*j* can be adjusted in length to accommodate differences in the size of a pelvic region H of a person to wear the changeable diaper 3.

The tightening strip portions 3*g*, 3*h* are attached with magic tapes 3*i*, 3*j* in the respective left and right corresponding positions, as shown in FIGS. 1 and 14. The strip portions 3*g* and 3*h* thus serve as a belt to wear the diaper cup main body 2 on a pelvic region H of a sick person or the like. The changeable diaper 3 also comprises a surface cloth 3*m*, a lining cloth 3*n*, and an absorbent mesh cloth (not shown) interposed between the surface cloth 3*m* and the lining cloth 3*n*. The mesh cloth comprises a nylon cloth improved in absorbability, for example, by increasing the in-cloth space. The surface cloth 3*m* and the lining cloth 3*n* are sewed with dense cloth fiber, as compared to the mesh cloth.

Figure 16:
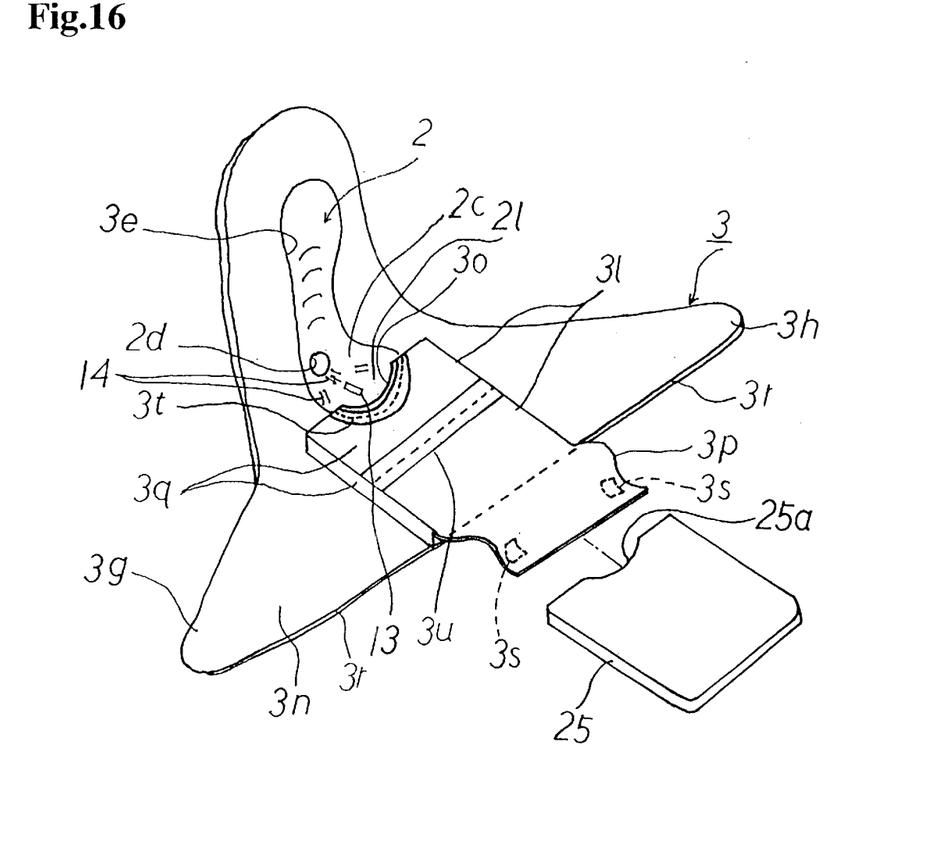
FIG. 16 is a perspective view showing a state when assembling the buffer member to the changeable diaper of the invention.
Figure 17:
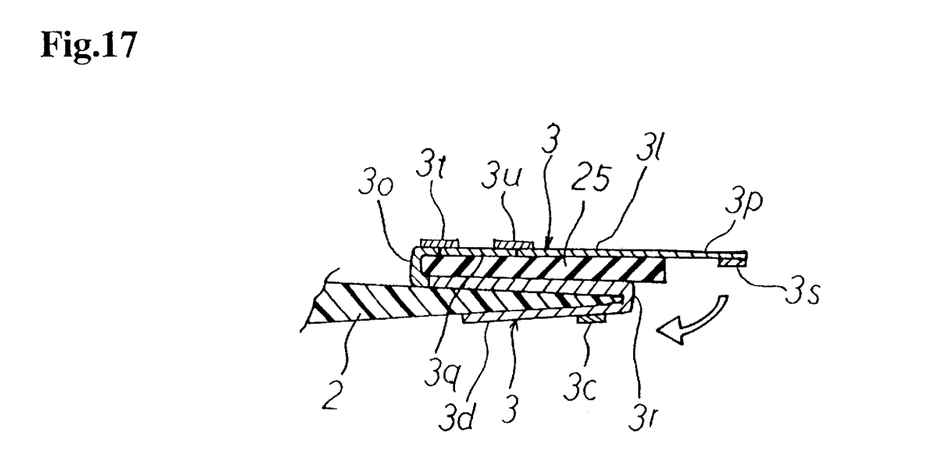
FIG. 17 is a sectional view showing a setup state of the buffer member of the invention.

Incidentally, in the changeable diaper 3, where a waterproof dam 23 is not provided in the diaper cup unit 1, an apron 3*o* is provided formed of a waterproof cloth in an edge on a bag 3*l* side of the elongate hole 3*e*. The apron 3*o* extends from the support portion 15*a* of the waist-fit seat 15 into the diaper cup main body 2, as shown in FIGS. 8, 16 and 18. This prevents wash water or urine from leaking through between the waist-fit seat 15 in a peripheral position of the apron 3*o* and the changeable diaper 3.

Figure 20:
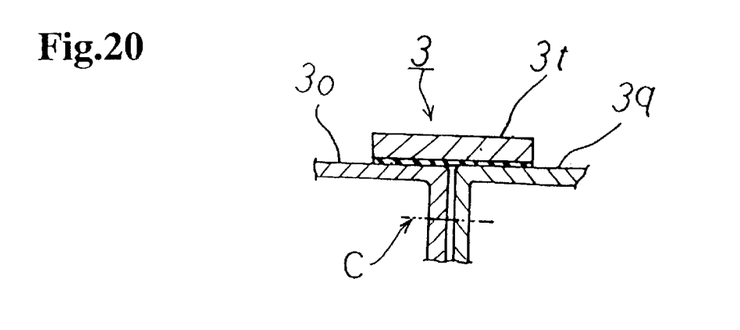
FIG. 20 is a sectional view showing a setup state of a waterproof sheet of the invention.

As shown in FIGS. 16, 18 and 20, water preventive sheets 3*t*, 3*u* are bonded on a seam C between the apron 3*o* and the bag 3*l* and a seam between the waterproof cloth 3*q* and the bag 3*l*. This prevents water from leaking through the seam of the apron 3*o* and the bag 3*l* or a seam of the waterproof cloth 3*q* and the bag 3*l*.

Figure 15:
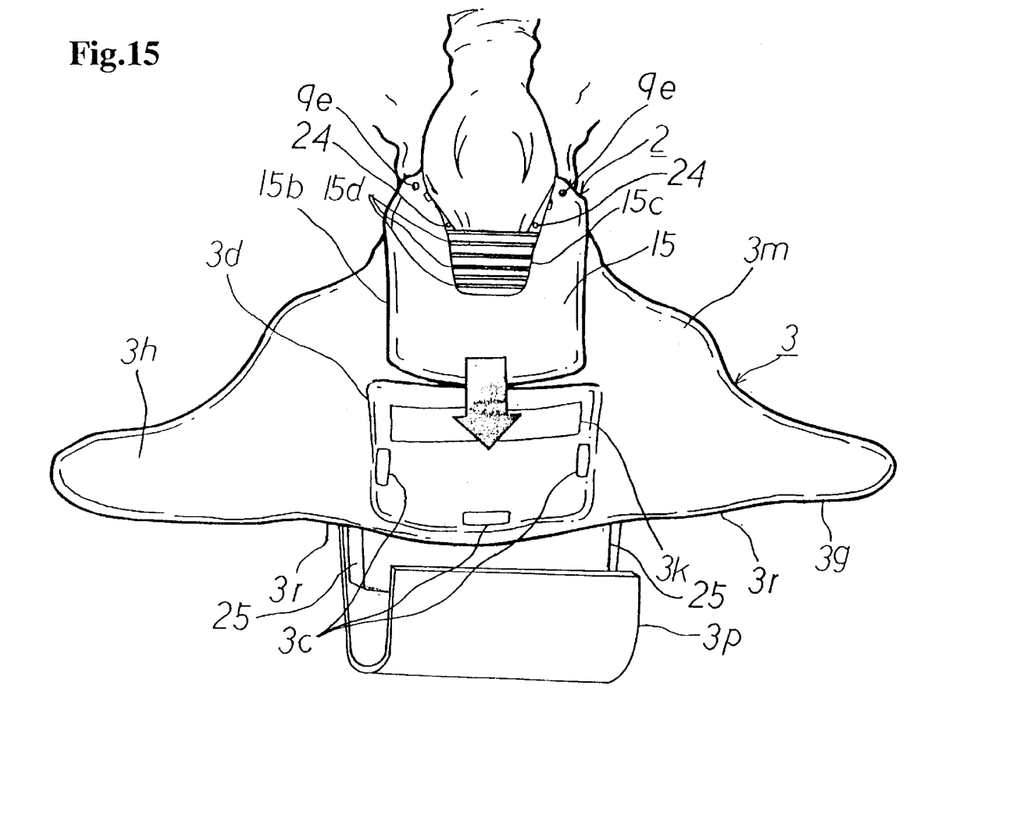
FIG. 15 is a front view showing a state when assembling the waist-fit seat to the changeable diaper of the invention.

The changeable diaper 3 has a bag 3*d* on its backside into which the plate-like portion 15*b* of the waist-fit seat 15 is inserted, as shown in FIG. 15. By inserting the plate-like portion 15*b* of the seat, the changeable diaper 3 is prevented against rumples due to the rigidity of the plate-like portion 15*b*. Thus, the skin of a sick person or the like will be contacted with a stretched state of the changeable diaper 3 without rumples, thereby preventing irritation of the sick person's skin. The bag 3*l* for inserting the buffer member 25 is formed on a surface side of the changeable diaper 3 to be contacted with a pelvic region H, as shown in FIGS. 1, 14, 16 and 17.

The bag 3*l* has a close cover 3*p* for covering an insertion port for inserting the buffer member 25. The buffer member 25 can be fixed in the bag 3*l* by covering the close cover 3*p* and joining the magic tape 3*s* to the magic tape 3*c* on the surface side, as shown in FIG. 16. The side surface and the elongate side 3*e* of the bag 31 comprises a waterproof cloth 3*q*.

The buffer member 25 comprises a gel sheet that can receive dispersedly a body weight of a sick person or the like. This prevents bedsores of the sick person or the like. The buffer member 25 comprises, for example, a soft, thick plate (available, for example, under the trademark ACTIONPAD). The plate for the buffer member 25 is selected so that it will not have a reaction force upon undergoing a weight, which is free from adhesion at its bottom, and has a pressure-dispersion effect. The plate is soft and ready to deform upon undergoing load, but has an excellent restoration force. The plate also helps to prevent sultry feeling caused by the device, and does not irritate the skin.

The buffer member 25 and bag 3*l* at one end close to the cavity 2*c* are formed with a cutout portion 25*a* in an arcuate form matched to the shape of the dam portion 23*d* of the waterproof dam 23, as shown in FIG. 16. The other end of the buffer member 25 is formed long to extend from the upper end 3*r*, as shown in FIGS. 1, 14 and 16. This shape prevents the upper end 3*r* of the changeable diaper 3 from pressing against a sick person or the like and irritating the skin.

The diaper cover 4 of the invention will now be described. As shown in FIGS. 1 and 14, the diaper cover 4 has magic tapes 4*a*, 4*b*, 4*c*, 4*d*, 4*e*, 4*i*, 4*j*, a fastener 4*f*, a hose-unit pass hole 4*g*, and a hose-unit enclosure portion (not shown).

The diaper cover 4 is generally in a T-form similar to the changeable diaper 3. The diaper cover 4 is a cloth member comprising a pelvic-region enclosure portion 4*k* to cover the enclosure portion 3*f*, and wrap portions 4*m*, 4*n* that correspond generally to the tightening strip portion 3*g*, 3*h*. The diaper cover 4 has a cut portion 4*p* extending from the hose-unit enclosure portion to the hose-unit pass hole 4*g*. The cut portion 4*p* separates the diaper cover 4 to its outer side. The fastener 4*f* is arranged in the cut portion 4*p* to close the cut portion 4*p* when the device is assembled.

The diaper cover 4 and the changeable diaper 3 are attached together by joining the magic tape 4*a* on the diaper cover 4 to the magic tape 3*c* on the changeable diaper 3. The diaper cover 4 itself is fixed on a human body by joining the magic tapes 4*a*, 4*b*, 4*c*, 4*e*, 4*i*, 4*j* to the diaper cover 4, which is preferably made of a French-pile cloth. The fastener 4*f* is provided so that the fastener 4*f* can be opened to take out only the diaper cover 4 when the diaper cup main body 2 is connected with the hose connecting portion 2*u*.

The pelvic-region enclosure portion 4*k* is made for free movement by separating from the hose-unit enclosure portion below the hose-unit pass hole 4*g* to an upper end and sewing a fastener 4*f* thereon. The hose-unit pass hole 4*g* is an elongate hole coincident with the hose connecting portion 2*u* of the diaper main body 2 and made long along a centerline of the diaper cover 4.

The hose-unit enclosure portion is in a cylindrical form and is provided continuous with the hose-unit pass hole to cover and hide the hose connecting portion 2*u*. The hose-unit enclosure portion has a fastener 4*f* arranged longitudinally in a front center, as shown in FIGS. 1 and 14, so that the cylindrical hose-unit enclosure portion can be opened by opening the fastener 4*f*.

On an upper rear side of the diaper cover 4, an expansion-and-contraction rubber 4*q* is internally provided, as shown in FIG. 1, so that the upper end of the diaper cover 4 fits a waist region of a human body. Also, a waist fit strip 4*r* is arranged as a cushion member in a generally center portion of the diaper cover 4.

With the diaper cup main body 2, changeable diaper 3 and diaper cover 4 explained above, the changeable diaper 3 and diaper cup main body 2 are fastened together by the hooks 9*a*, 9*b*, 9*c*, 9*d*, 9*e*, 3*b*. Next, the changeable diaper 3 and the diaper cover 4 are fastened together by the magic tapes 3*c*, 3*i*, 3*j*, 4*a*, 4*b*, 4*c*, 4*e*, 4*i*, 4*j*. Thus, a diaper cup unit 1 is completed as shown in FIG. 14.

In the diaper cup unit 1, the hose unit 29 is connected to the hose connecting portion 2*u*, as shown in FIG. 11. The hose unit 29 connects the diaper cup unit 1 to external equipment, which has the excrement absorbing hose 16, wash-water feed hose 17, air feed hose 18 and sensor coupler 2*k* in one body, and collectively supports them. The hose unit 29 is free to attach to and detach from the hose connecting portion 2*u* positioned in the underside of the diaper cup main body 2. A hold piece 28 is fixed to hardware (not shown) on a side of the diaper cup main body 2. A hose cover 5 is continuous with and overlaps the hose-unit enclosure portion (not shown) of the diaper cover 4.

The present invention having the above structure and operation provides the following effects:

According to the present invention, a device for disposing excrement is provided having a diaper cup main body for enclosing a pelvic region of a human body, a discharge port for discharging excrement excreted in the diaper cup main body, a sensor for detecting the excrement excreted in the diaper cup main body, and a changeable diaper removably provided on the diaper cup main body. The device for disposing excrement is characterized by a buffer member interposed between a pelvic region of a human body and the diaper cup main body. The buffer member prevents irritation of the skin of a sick person or the like due to his or her body weight wearing the diaper cup main body. Thus, an excrement disposal apparatus is provided that does not cause pain even when the diaper cup main body is worn for a long time.

The diaper cup main body has a cavity formed in a surface on a side to be fit on a pelvic region of a human body to put a human body in a non-contact state. The buffer member is laid in a peripheral material of the cavity of the diaper cup main body beneath a pelvic region of a human body. This makes it possible to retain a location loaded with a pelvic-region body weight by a required minimum buffer member. The changeable diaper can be thin in the diaper interior entirely, reducing the feeling of physical discomfort due to the diaper cup main body having the buffer member worn by a sick person or the like while sleeping.

The buffer member comprises a thick plate member. This makes it possible to increase the cushion effect and prevent irritation of the skin.

The buffer member comprises a gel soft material. This makes it possible to dispersedly sustain a body weight of a sick person or the like, thereby preventing bedsores. This also makes it possible to prevent the excreted urine or the like from leaking to an outside of the diaper cup main body due to close contact without a gap between the buffer member and the diaper cup main body or changeable diaper.

The diaper cup main body has a waist-fit seat generally in a plate form provided continuous with an upper end thereof. The buffer member is provided on an upper position of the waste-fit seat. This makes it possible not to immediately contact the comparatively hard, waist-fit seat placed under a waist of a sick person or the like, providing a comfortable device for disposing excrement without a feeling of pain.

The buffer member projects at an upper end of the changeable diaper on a back side of a human body. This makes it possible to cover a step due to a thickness of an upper end of the changeable diaper by the buffer member, thereby preventing irritation of the skin.

The buffer member is inserted in a bag provided on an inner side of the changeable diaper to be fit on a human body. This makes it possible to prevent wrinkling in the portion of the changeable diaper to be contacted with a pelvic region on a back side of a sick person or the like wearing the diaper cup, thereby preventing skin irritation caused by pressing such wrinkles on the skin due to a body weight or the like. Also, the buffer member can receive the body weight of the sick person or the like substantially directly, thereby improving the feeling of the diaper cup during use.

The bag of the changeable diaper into which the buffer member is inserted is formed by a waterproof cloth on a side of the cavity. This makes it possible to improve the waterproof qualities of the bag and thereby prevent soiling of the diaper cover or sheets around the changeable diaper.

The bag of the changeable diaper into which the buffer member is inserted is arranged with a waterproof sheet in a seam of the waterproof cloth. This makes it possible to prevent water content from intruding through a seam of the bag into the changeable diaper. Thus, the changeable diaper does not have an uncomfortable wet feeling for the sick person or the like.

The bag of the changeable diaper into which the buffer member is inserted is provided with a magic tape and has a close cover to close an opening. This makes it possible to facilitate putting the buffer member into and out of the bag. Thus, when the diaper is tainted or moistened, the buffer member can be easily taken out of the bag to wash the changeable diaper or buffer member.

What is claimed is:

1. A device for disposing excrement comprising:
   a diaper cup main body for enclosing a pelvic region of a human body;
   a discharge port for discharging excrement excreted in the diaper cup main body;
   a sensor for detecting the excrement excreted in the diaper cup main body;
   a changeable diaper removably provided on the diaper cup main body; and
   a buffer member interposed between a pelvic region of a human body and said diaper cup main body, wherein said buffer member is inserted in a pocket provided on an inner side of said changeable diaper.

2. A device for disposing excrement as claimed in claim 1, wherein said diaper cup main body has a cavity formed in a surface thereof on a side to be fit on a pelvic region of a human body to put a human body in a non-contact state, and
   said buffer member is laid in a peripheral material of said cavity of said diaper cup main body beneath a pelvic region of a human body.

3. A device for disposing excrement as claimed in claim 1, wherein said buffer member comprises a thick plate member.

4. A device for disposing excrement as claimed in claim 1, wherein said buffer member comprises a gel soft material.

5. A device for disposing excrement as claimed in claim 1, wherein said diaper cup main body has a waist-fit seat generally in a plate form provided continuous with an upper end thereof, and
   said buffer member is provided on an upper portion of said waist-fit seat.

6. A device for disposing excrement as claimed in claim 1, wherein said buffer member projects at an upper end of said changeable diaper on a back side of a human body.

7. A device for disposing excrement as claimed in claim 1, wherein said diaper cup main body has a cavity formed in a surface thereof on a side to be fit on a pelvic region of a human body, and
   said pocket of said changeable diaper into which said buffer member is inserted is formed by a waterproof cloth on a side of said cavity.

8. A device for disposing excrement as claimed in claim 7, wherein said pocket of said changeable diaper into which said buffer member is inserted has a waterproof sheet in a seam of said waterproof cloth.

9. A device for disposing excrement as claimed in claim 1, wherein said pocket of said changeable diaper into which said buffer member is inserted has a fastener strip and has a close cover to close an opening.

10. A device for disposing excrement comprising:
    a diaper cup main body for enclosing a pelvic region of a human body;
    a discharge port for discharging excrement excreted in the diaper cup main body;
    a sensor for detecting the excrement excreted in the diaper cup main body;
    a changeable diaper removably provided on the diaper cup main body, said changeable diaper having a pocket; and
    a buffer member disposed within said pocket of said changeable diaper, said buffer member being adapted to be interposed between a pelvic region of a human body and said diaper cup main body, said buffer member comprising a plate formed of a soft gel material;
    wherein said pocket is formed on a front side of said changeable diaper, and said changeable diaper further comprises another pocket formed on a backside thereof for accommodating a plate-like portion of a waist-fit seat.

11. The device for disposing excrement according to claim 10, wherein said changeable diaper has a cover for closing an open side of said pocket, and a fastening means for securing the cover in a closed position with said buffer member contained in said pocket.

12. The device for disposing excrement according to claim 10, wherein said buffer member has a generally rectangular shape with an arcuate cutout portion formed in one side for accommodating a similarly shaped portion of said diaper cup main body.

* * * * *